United States Patent [19]

Thompson et al.

[11] Patent Number: 4,633,019

[45] Date of Patent: Dec. 30, 1986

[54] α-AMINOALKYLSULFUR COMPOSITIONS

[75] Inventors: Neil E. S. Thompson, Creve Coeur; Derek Redmore, Webster Groves; Bernardus A. O. Alink, St. Louis, all of Mo.

[73] Assignee: Petrolite Corporation, St. Louis, Mo.

[21] Appl. No.: 611,579

[22] Filed: May 18, 1984

Related U.S. Application Data

[63] Continuation of Ser. No. 301,620, Sep. 14, 1981, abandoned.

[51] Int. Cl.[4] .......... C07C 149/24

[52] U.S. Cl. .......... 564/501; 564/1; 564/462

[58] Field of Search .......... 564/501, 500, 462, 1

[56] References Cited

U.S. PATENT DOCUMENTS 4,285,984 8/1981 Huber .......... 426/535

FOREIGN PATENT DOCUMENTS 2310141 9/1974 Fed. Rep. of Germany .......... 564/501

2010024 2/1970 France .......... 504/291

109093 9/1976 Japan .

OTHER PUBLICATIONS

Egutkin, Issled. Obl. Khim. Vysokomol. Soedin. Neftekhim., 1977, Chemical Abstracts, vol. 92, p. 412, No. 170103c (1980).

*Primary Examiner*—Robert Gerstl

*Attorney, Agent, or Firm*—Sidney B. Ring; Leon Zitver

[57] ABSTRACT

This invention relates to α-aminoalkylsulfur compositions and to the preparation and uses thereof, particularly as corrosion inhibitors. These compositions contain a moiety of the general formula

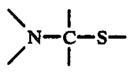

in a linear or cyclic configuration.

4 Claims, No Drawings

α-AMINOALKYLSULFUR COMPOSITIONS

This is a continuation of application Ser. No. 301,620, filed Sept. 14, 1981, now abandoned.

This invention relates to α-aminoalkylsulfur compositions, to the preparation thereof, and to uses thereof, particularly as corrosion inhibitors.

These α-aminoalkylsulfur compositions contain a moiety of the general formula

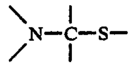

in a linear or cyclic configuration.

One group of such compositions are described as α-amino alkylsulfides and can be represented by the general formula:

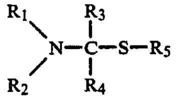

In this formula the R groups which can be the same or different are H, a hydrocarbon or substituted hydrocarbon group such as alkyl, aryl, etc., for example methyl, ethyl, propyl, etc., etc. The various R groups can also be joined to form rings, e.g., $R_1$ and $R_2$, $R_1$ and $R_3$, $R_1$ and $R_5$, etc.

These compositions may be prepared by a wide variety of methods. These are outlined as follows.

A particularly effective method of preparation of these products involves the interaction of an amine, an aldehyde or ketone and a thiol as depicted in Equation 1.

Equation 1

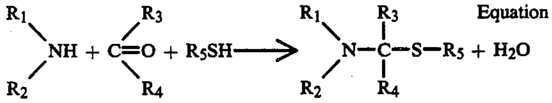

The reaction can be carried out with or without solvent such as alcohols, hydrocarbons etc. at temperatures from 0°-200° C. Preferred temperatures are in the range of 20°-80°. The amine component can be primary or secondary i.e. $R_1$ is alkyl or aryl and $R_2$ is H or both $R_1$ and $R_2$ can be cyclic such as pyrrolidine, morpholine, piperidine, etc., $R_1$ can be methyl, ethyl, propyl, butyl, hexyl, octyl, decyl, dodecyl, tetradecyl, hexadecyl, octadecyl, etc. $R_2$ can have similar structures including H, etc.

The carbonyl component can be an aldehyde or ketone. $R_3$ and $R_4$ can be the same or different including H, alkyl such as methyl, ethyl, propyl, isopropyl, butyl, etc.

The R of the thiol component i.e., $R_5$ can vary widely, including alkyl group such as methyl, ethyl, propyl, butyl, pentyl, hexyl, heptyl, octyl, nonyl, decyl, undecyl, dodecyl, tetradecyl, hexadecyl, octadecyl, etc. Branched alkyl groups can also be used.

An alternative procedure is depicted in Equation 2 in which a thiol is added to a Schiff Base or imine.

Equation 2

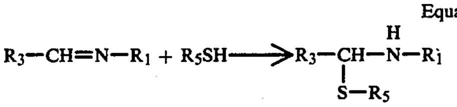

The possible variations in the R groups are similar to those in Equation 1.

A further method which yields cyclic products is shown in which Equation 3 in the amine and thiol functions are contained in the same molecule.

Equation 3

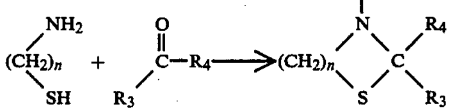

n = 2,3

An additional preparative method which also yields cyclic products is described in Equation 4. In this procedure sulfur interacts with the carbonyl compound to generate the C-S-H group. Several examples of this method have been described in the literature e.g. F. Asinger and M. Thiele, Angew. Chem., 70, 667(1958), F. Asinger et al, W. Leuchtenberger, Annalen, 615, 84(1958) and references cited therein, F. Ansinger and W. Leuchtenberger, Annalen, 1183 (1974).

Equation 4

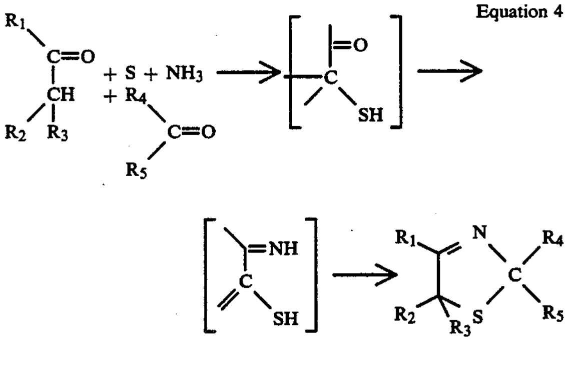

In the simplest examples

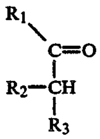 is 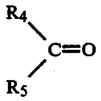

For example in the specific case of cyclohexanone the reaction is as follows:

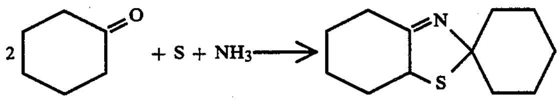

A useful extension of this process is to use a substoichiometric amount of sulfur which leads to a mixture of products which can be particularly advantageous. If, for example, cyclohexanone, ammonia and less than an equivalent of sulfur are reacted, a mixture shown in Equation 5 is obtained. Further heating can lead to partial deammoniation as shown in equation 6. The procedures involving carbonyl compounds and ammonia (without sulfur) are disclosed in U.S. Pat. Nos. 3,931,191, 3,904,625 and 4,113,730.

Equation 5

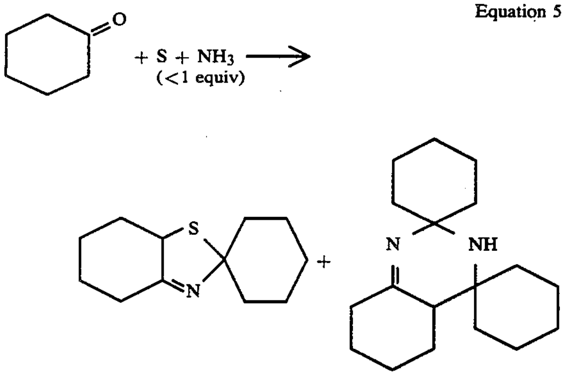

Equation 6

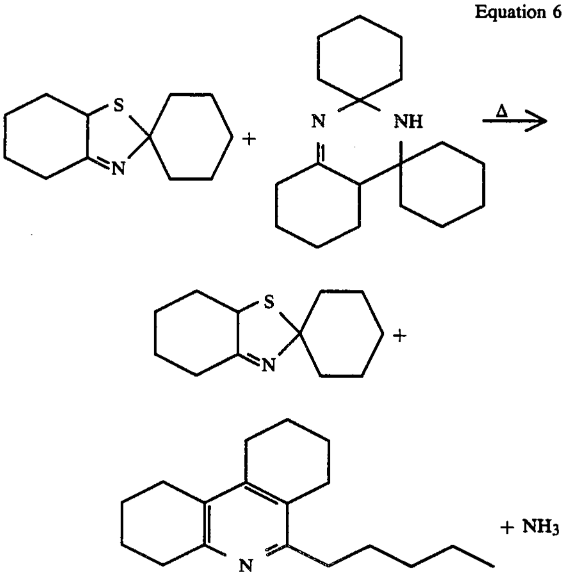

A general reference to the preparation of the structure in this disclosure, can be found in H. Hellmann and G. Opitz, α-Aminoalkylierung, Verlag-Chemie GMBH, Weinheim/Bergstr. 1960.

The following examples are presented for purposes of illustration and not of limitation.

EXAMPLE 1

Reaction product of a secondary amine

To a 40% aqueous solution of dimethylamine (12 ml; 0.1 mole) cooled in an ice bath was added aqueous 37% formaldehyde (10 ml; 0.13 mole) dropwise during 30 minutes. To this mixture was added dodecylthiol (20 g; 0.1 mole) in one portion and stirring was continued for one hour. After saturation with potassium carbonate the organic phase was separated. The product was identified as shown in the formula below:

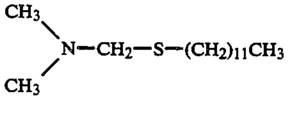

EXAMPLE 2

Reaction Product of secondary amine

Diethylamine (7.3 g; 0.1 mole) was dissolved in isopropanol (20 g), cooled in an ice bath and stirred during the addition of 37% formaldehyde (10 ml; 0.13 mole). To this solution was added octylthiol (14.6 g; 0.1 mole) in one portion and the mixture stirred to give a homogeneous solution of the desired aminomethylated thiol of the formula below:

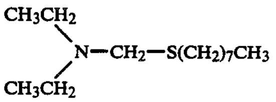

EXAMPLE 3

Reaction product of a primary amine

To a solution of octylamine (13 g; 0.1 mole) in isopropanol (68 g) cooled in an ice bath was added aqueous formaldehyde (10 ml; 0.13 mole) during 20 mins with efficient stirring. Dodecylthiol (20 g; 0.1 mole) was added and the reaction completed by stirring at ambient temperature for 1 hour. The product is represented by the following formula:

$CH_3(CH_2)_7-N-CH_2-S-(CH_2)_{11}CH_3$
H

To avoid unnecessary repetition the following table summarizes additional examples prepared by the method of Examples 2 and 3.

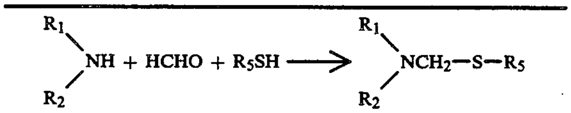

| Example | $R_1$ | $R_2$ | $R_5$ |
|---|---|---|---|
| 4 | $CH_3CH_2$— | $CH_3CH_2$— | $CH_3(CH_2)_{11}$— |
| 5 | $HOCH_2CH_2$— | $HOCH_2CH_2$— | $CH_3(CH_2)_7$— |
| 6 | $CH_3CH_2CH_2$ | $CH_3CH_2CH_2$— | $CH_3(CH_2)_7$— |
| 7 | $CH_3CH_2CH_2$— | $CH_3CH_2CH_2$— | $CH_3(CH_2)_{11}$— |
| 8 | $HOCH_2CH_2$— | $HOCH_2CH_2$— | $CH_3(CH_2)_{11}$— |
| 9 | $CH_3(CH_2)_3$— | $CH_3(CH_2)_3$— | $CH_3(CH_2)_{11}$— |
| 10 | $-CH_2CH_2-O-CH_2CH_2-$ | ($R_1$ & $R_2$ joined to form ring) | $CH_3(CH_2)_{11}$— |
| 11 | $-(CH_2)_5-$ | | $CH_3(CH_2)_{11}$— |
| 12 | $-(CH_2)_5-$ | | $CH_3(CH_2)_7$— |
| 13 | c$C_6H_{11}$— | c$C_6H_{11}$— | $CH_3(CH_2)_{11}$— |
| 14 | c$C_6H_{11}$— | c$C_6H_{11}$— | $CH_3(CH_2)_7$— |
| 15 | $CH_3(CH_2)_3$— | H | $CH_3(CH_2)_{11}$— |
| 16 | $CH_3(CH_2)_{11}$— | H | $CH_3(CH_2)_{11}$— |
| 17 | Cocoalkyl— | Cocoalkyl— | $CH_3(CH_2)_{11}$— |

c means cyclic

The following examples illustrate the use of polyamines and hydroxyalkyl polyamines.

EXAMPLE 18

Diethylene triamine (10.3 g; 0.1 mole) was dissolved in isopropanol (60 g) and after cooling to 5°-10° C. was stirred during the addition of 37% aqueous formaldehyde (10 ml; 0.13 mole To this solution was added dodecylthiol (20.2 g; 0.1 mole) and the reaction completed by stirring one hour at 30° C. The product is aminomethylated thiol represented by the formula below:

$C_{12}H_{25}S—CH_2—(C_4H_{12}N_3)$

EXAMPLE 19

Hydroxyethylethylenediamine (10.4; 0.1 mole) was dissolved in isopropanol (60 g) and cooled to 5° C. before the dropwise addition of 37% aqueous formaldehyde (10 ml; 0.13 mole) during 20 mins. While stirring was continued dodecylthiol (20.2 g; 0.1 mole) was added and the reaction completed in 1 hour at ambient temperature.

The product is represented by the following formula:

$C_{12}H_{25}—SCH_2—(C_4H_{11}N_2O)$

EXAMPLE 20

Triethylenetetramine ethoxylated with 2 moles of ethylene oxide (23.4 g; 0.1 mole) was dissolved in isopropanol (39 g), cooled to 5°-10° C. and treated, dropwise, with 37% aqueous formaldehyde (10 ml; 0.13 mole). While continuing to stir dodecylthiol (20.2 g; 0.1 mole) was added and the reaction completed at ambient temperature in one hour. The product is represented by the formula below:

$CH_2CH_2OH$ $C_{12}H_{25}—S—CH_2—[(C_6H_{15}N_4)]$ $CH_2CH_2OH$

EXAMPLE 21

In a manner similar to that of Example 20 triethylenetetramine propoxylated with two moles of propylene oxide was reacted in sequence with formaldehyde and dodecylthiol. The product is represented by the formula below:

$C_{12}H_{25}—S—CH_2—(C_6H_{15}N_4)(CH_2—CH(CH_3)OH)_2$

The following examples illustrate the use of higher aldehydes.

EXAMPLE 22

To a solution of n-butylamine (8 g; 0.11 mole) in isopropanol (66 g) at 5°-10° C. was added butyraldehyde (8 g; 0.11 mole) with stirring. After 30 mins. dodecylthiol (20 g; 0.1 mole) was added and the mixture stirred at ambient temperature for one hour.

The product is represented by the formula below:

H $C_{12}H_{25}—S—CH—N—(CH_2)_2CH_3$ $(CH_2)_2CH_3$

Further examples utilizing the procedure of Example 22 are summarized in the following table:

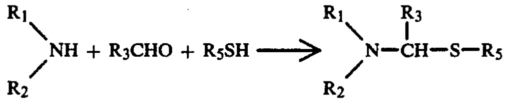

| Example No. | $R_1$ | $R_2$ | $R_3$ | $R_5$ |
|---|---|---|---|---|
| 23 | $CH_3(CH_2)_3—$ | H | $CH_3(CH_2)_2—$ | $CH_3(CH_2)_7—$ |
| 24 | $CH_3(CH_2)_5—$ | H | $CH_3(CH_2)_2—$ | $CH_3(CH_2)_7—$ |
| 25 | $CH_3(CH_2)_6—$ | H | $CH_3(CH_2)_2—$ | $CH_3(CH_2)_{11}—$ |
| 26 | $HOCH_2CH_2—$ | H | $CH_3(CH_2)_2—$ | $CH_3(CH_2)_{11}—$ |
| 27 | $\underline{c}C_6H_{11}—$ | H | $CH_3(CH_2)_2—$ | $CH_3(CH_2)_{11}—$ |
| 28 | $CH_3(CH_2)_7—$ | H | $CH_3(CH_2)_2—$ | $CH_3(CH_2)_{11}—$ |
| 29 | $CH_3(CH_2)_{11}—$ | H | $CH_3(CH_2)_2—$ | $CH_3(CH_2)_{11}—$ |
| 30 | $\underline{t}C_4H_9—$ | H | $(CH_3)_2CH—$ | $\underline{t}C_{12}H_{25}—$ |
| 31 | $NH_2CH_2CH_2—$ | H | $CH_3(CH_2)_2—$ | $CH_3(CH_2)_7—$ |
| 32 | $HO(CH_2)_2NH(CH_2)_2—$ | H | $CH_3(CH_2)_2—$ | $CH_3(CH_2)_7—$ |

Products containing the N-C-S grouping in a ring.

EXAMPLE 33

2,2-Pentamethylene-4,5-tetramethylene-$\Delta^3$-thiazoline

Sulfur (32 g; 1 mole) was suspended in cyclohexanone (196 g; 2 mole) by vigorous stirring in a sealed reactor while gaseous ammonia was introduced. Cooling was applied as necessary to keep the temperature between 40°-50° C. Ammonia was added at a rate such that a pressure of 25-30 psi was maintained. The uptake of ammonia ceased after 2-3 hours. Stirring was discontinued and aqueous phase separated and discarded. Distillation of the organic phase yielded 2,2-pentamethylene-4,5-tetramethylene-$\Delta^3$-thiazoline.

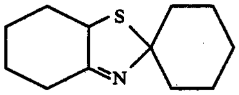

The product was characterized by infrared and nuclear magnetic resonance spectra.

EXAMPLE 34

(a) The reaction between cyclohexanone/ammonia and less than 1 equivalent of sulfur Cyclohexanone (200 g; 2.04 mole), sulfur (10 g; 0.31 mole) and ammonium nitrate (10 g; 0.13 mole) were placed in a pressure reactor and, while stirring, ammonia gas was added. A pressure of 30-40 psi was maintained with the reaction temperature between 50°-60° C. Ammonia uptake ceased at approximately 16 hrs. Stirring was stopped and the upper aqueous phase which separated discarded. The infrared spectrum shows a strong C═N peak at 6.05μ from the tetrahydropyrimidine and thiazoline.

(b) Conversion of the tetrahydropyrimidine component to pyridine

The organic phase of 34(a) is then charged to a 500 ml reactor equipped with stirrer, thermometer and reflux condenser attached to a Dean Stark trap. Nitric acid (4 g) was carefully added and the mixture gradually heated to 190°-200° C. for 5-6 hours, while removing any water or low boiling by products. The progress of the reaction was followed by the decrease in the off gas evolution and by the change in infrared spectral characteristics, the peak at 6.02μ, —C≡N—, disappears and a strong peak at 6.40μ (pyridine) appears.

The product gave the following analysis; S, 5.2%, N, 5.15%. Gas chromatography showed the product contained the two compounds below as major components in the ratios shown:

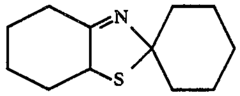

33%

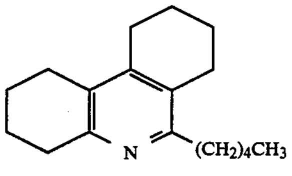

67%

EXAMPLE 35

A cyclohexanone/ammonia/sulfur reaction with less than 1 equivalent of sulfur

This example follows the procedure of example 34 using cyclohexanone (200 g; 2.04 mole), sulfur (20 g; 0.625 mole). The product is similar to the previous example except that the ratio of thiazoline to phenanthridine is 13:7.

In summary, the invention relates to compositions characterized by the presence of the following moiety

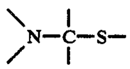

The compositions containing this moiety may be linear, such as illustrated in the following formula

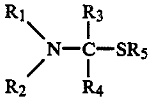

where the R's are hydrocarbon such as alkyl, aryl, substituted derivatives thereof, or H.

In the preferred linear embodiments $R_1$, and $R_5$ are alkyl or substituted alkyl, and $R_2$ is alkyl or hydrogen; $R_3$ is hydrogen and $R_4$ is either hydrogen or alkyl. $R_1$ and $R_2$ may also be joined to form an amino-containing ring such as

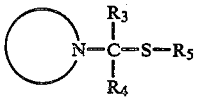

but preferably

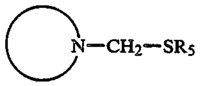

Where the composition is derived from a polyamine the composition may be represented by the formula $R_5$—S—$CH_2$— N where N represents a polyamine moiety.

The

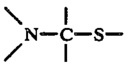

moiety may be part of a ring structure such as represented by the following thiazoline structure

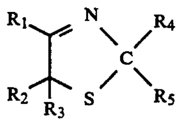

where $R_1$, $R_2$, $R_3$, $R_4$, $R_5$ are hydrocarbon groups such as alkyl, aryl, or hydrogen.

$R_1$ and $R_2$ and $R_4$ and $R_5$ may also be joined in a cyclic structure as represented below

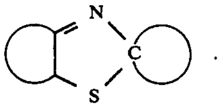

Where thiazolines are formed by reacting the carbonyl with ammonia and an equivalent of S, one obtains primarily the thiazoline, for example

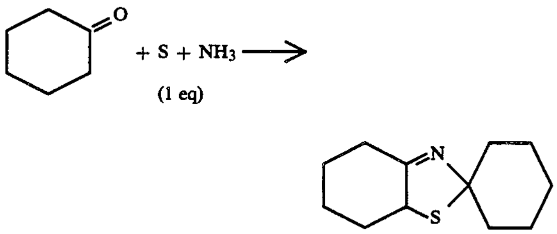

Where one reacts the carbonyl with less than an equivalent of S, one obtains a mixture of the thiazoline and the tetrahydropyrimidine, for example

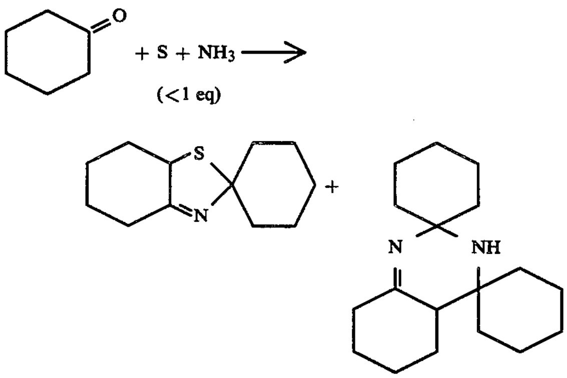

On further heating the tetrahydropyrimidine formed can be deammoniated to phenanthridene as illustrated by the following

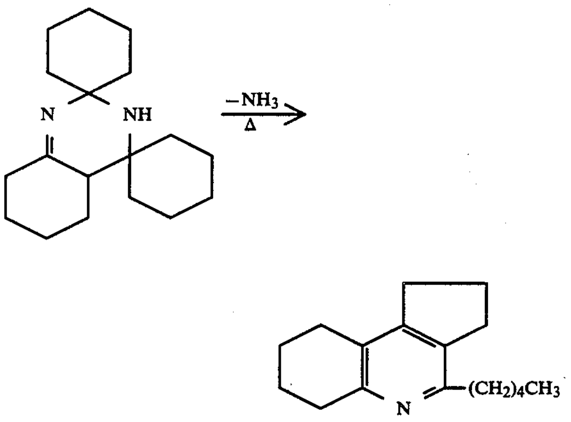

The above compositions are prepared according to the following reactions:

I

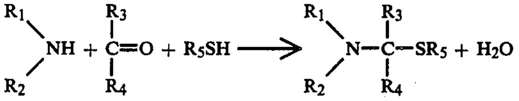

II

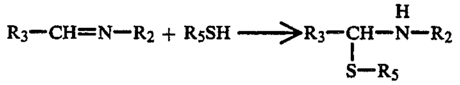

III

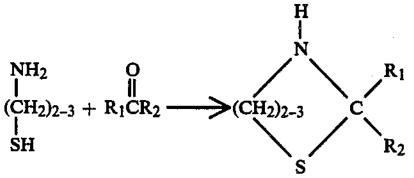

IV

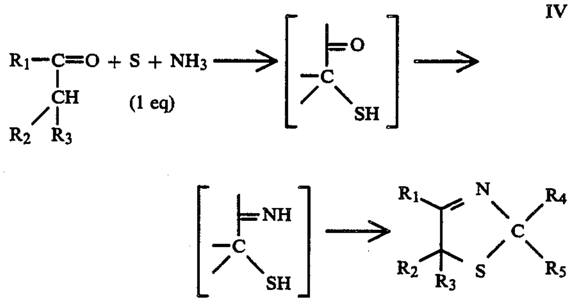

For example

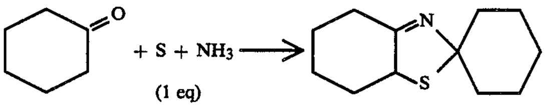

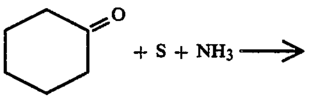

-continued

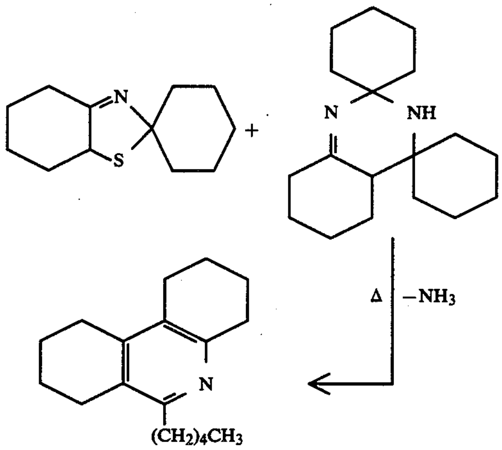

The compositions of this invention are useful as corrosion inhibitors, particularly in acid solutions and brines.

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc. for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the compounds of this invention, for example at least about 5 p.p.m., such as from about 50 to 50,000 p.p.m., from about 100–30,000 p.p.m., but preferably from about 200 to 10,000 p.p.m.

Ferrous metal articles are pickled by contacting the surface (usually by immersion in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas beating formation. The treating acid, commonly a mineral acid such as HCl, is capable of forming water soluble salts upon contact with the formation and is effective to increase the permeability thereof and augment the flow of petroleum to the producing well.

Application in which the inhibitors of the present invention are particularly useful include oil-well acidizing solutions, metal pickling, cleaning and polishing baths, boiler cleaning compositions and the like. They are also useful as oil soluble corrosion inhibitors, bactericides, water-in-oil demulsifying agents, surfactants and the like.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system". If the water is recirculated in a closed system without substantial aeration, the secondary recovery method is referred to herein as a "closed water flooding system."

Because of the corrosive nature of oil field brines, to economically produce oil by water flooding it is necessary to prevent or reduce corrosion since corrosion increases the cost thereof by making it necessary to repair and replace such equipment at frequent intervals.

We have now discovered a method of preventing corrosion in systems containing a corrosive aqueous media, and most particularly in systems containing brines, which is characterized by employing the compositions of this invention.

We have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analagous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoid, it is quite important to use as little as possible of these compounds consistent with optimum corrosion inhibition. Optimum performance is generally obtained employing about 1,000 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

The following examples, which are presented by way of illustration and not of limitation, demonstrate the uses of the compositions of this invention.

CORROSION TEST RESULTS

$CO_2$/Brine Sparge Test

Corrosion tests were carried out at ambient temperature in 2% sodium chloride solution saturated with carbon dioxide. Corrosion rates were measured using PAIR meter of the type described in U.S. Pat. No. 3,406,101. Inhibitors were injected after the electrodes had been allowed to corrode for 2–4 hours.

Protection is calculated in the usual manner from corrosion rate ($R_1$) of fluids without inhibitor and corrosion rate ($R_2$) after 24 house in presence of particular inhibitor according to the formula, $$\frac{R_1 - R_2}{R_1} \times 100 = \text{Percent Protection.}$$

| | Corrosion Test Data | | |
|---|---|---|---|
| | Percent Protection at Concentration | | |
| Example | 25 ppm | 50 ppm | 100 ppm |
| Example 1 | 90 | 98 | 99 |
| Example 2 | 92 | 98 | 99 |
| Example 3 | 80 | 90 | 96 |
| Example 5 | 92 | 99 | 99 |
| Example 9 | 92 | 99 | 99 |
| Example 11 | 90 | 94 | 96 |
| Example 18 | 80 | 93 | 97 |
| Example 19 | 86 | 94 | 97 |
| Example 20 | 86 | 96 | 98 |
| Example 21 | 88 | 94 | 97 |
| Example 22 | 90 | 96 | 97 |

Acid Inhibitors test in Hydrochloric Acid 200 ml of 10% hydrochloric acid in a 300 ml beaker is heated to 165°–170° F. and the chemical to be tested is added at the appropriate concentration. Cleaned 1020 mild steel coupons ($\frac{7}{8} \times 3\frac{1}{4} \times 1/6''$) are weighed and then placed in the acid for exactly one hour. The coupons are removed and washed with hot water, hot acetone, air dried and then re-weighed.

Corrosion protection is calculated in the usual manner from the weight loss of the blank ($W_1$) and weight loss ($W_2$) in the presence of inhibitor according to the formula $$\frac{W_1 - W_2}{W_1} \times 100 = \text{Percent protection.}$$

The coupons used in corrosion experiments weighed 20.5–21 g and the typical weight loss without inhibitors was 4–5 gms.

| | Acid Inhibitor Tests | |
|---|---|---|
| Compound | Concentration, ppm | Protection |
| Example 1 | 250 | 93 |
| Example 2 | 250 | 96 |
| Example 3 | 250 | 96 |
| Example 5 | 250 | 95 |
| Example 9 | 250 | 97 |
| Example 11 | 250 | 94 |
| Example 18 | 250 | 96 |
| Example 19 | 250 | 97 |
| Example 20 | 250 | 96 |
| Example 21 | 250 | 96 |
| Example 22 | 250 | 95 |

Acid Inhibitors Test in Sulfuric Acid 200 ml of 10% sulfuric acid containing 10% iron in a 300 ml beaker is heated to 190° F. and the chemical to be tested is added at the appropriate concentration. Cleaned 1020 mild steel coupons ($\frac{7}{8}$"×$3\frac{1}{4}$×1/6") are weighed and then placed in the acid for exactly one hour. The coupons are removed and washed with hot water, hot acetone, air dried and then re-weighed.

Corrosion protection is calculated in the usual manner from the weight loss of the blank ($W_1$) and weight loss ($W_2$) in the presence of inhibitor according to the formula, $$\frac{W_1 - W_2}{W_1} \times 100 = \text{Percent Protection.}$$

The coupons used in corrosion experiments weighed 20.5-21 grams and the typical weight loss without inhibitors was 7-8 grams.

| | Sulfuric Acid Inhibitor Tests | |
|---|---|---|
| Compound | Concentration, ppm | % Protection |
| Example 2 | 1000 | 96 |
| Example 3 | 1000 | 94 |
| Example 5 | 1000 | 90 |
| Example 9 | 1000 | 93 |
| Example 18 | 1000 | 96 |
| Example 19 | 1000 | 95 |
| Example 20 | 1000 | 94 |
| Example 21 | 1000 | 96 |

-continued

| | Sulfuric Acid Inhibitor Tests | |
|---|---|---|
| Compound | Concentration, ppm | % Protection |
| Example 22 | 1000 | 89 |
| Example 33 | 1000 | 93 |
| Example 34 | 1000 | 97 |

We claim:

1. A compound of the formula

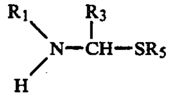

where $R_1$ is an alkyl, cycloalkyl or hydroxyalkyl group of 1 to 18 carbon atoms, $R_3$ is an alkyl group of 1 to 4 carbon atoms and $R_5$ is an alkyl group of 1 to 18 carbon atoms.

2. A compound of claim 1 wherein $R_1$ is alkyl.

3. The compound of claim 1 having the formula

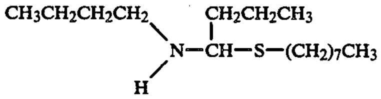

4. The compound of claim 1 having the formula

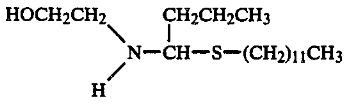

* * * * *